US007083809B2

(12) United States Patent
Iyer et al.

(10) Patent No.: US 7,083,809 B2
(45) Date of Patent: Aug. 1, 2006

(54) PURIFIED CYTOKINE INHIBITORY FACTOR

(75) Inventors: Subramanian Iyer, Hockessin, DE (US); William L. Johnson, Wilmington, DE (US); Lance Nguyen, Telford, PA (US); Steven C. Ross, Wilmington, DE (US); Ruye Xing, Avondale, PA (US)

(73) Assignee: Arkion Life Sciences, LLC, Wilmington, DE (US)

( * ) Notice: Subject to any disclaimer, the term of this patent is extended or adjusted under 35 U.S.C. 154(b) by 544 days.

(21) Appl. No.: 10/364,593

(22) Filed: Feb. 11, 2003

(65) Prior Publication Data

US 2003/0152641 A1 Aug. 14, 2003

Related U.S. Application Data

(60) Provisional application No. 60/356,038, filed on Feb. 11, 2002.

(51) Int. Cl.
*A61K 35/54* (2006.01)

(52) U.S. Cl. ...................................................... 424/581

(58) Field of Classification Search ................. 424/581
See application file for complete search history.

(56) References Cited

U.S. PATENT DOCUMENTS 4,357,272 A 11/1982 Polson
4,550,019 A 10/1985 Polson
4,748,018 A 5/1988 Stolle et al.
5,772,999 A 6/1998 Greenblatt et al.
6,420,337 B1 7/2002 Iyer et al.

FOREIGN PATENT DOCUMENTS

WO WO 00/43020 7/2000

OTHER PUBLICATIONS

Merriam Webster Online Dictionary "prevent" http://m-w.com/dictionary/preventing.*

R.S. Stephens et al. Genome sequence of an obligate intracellular pathogen of humans: *Chlamydia trachomatis*. Oct. 1998. Science 282:754-759.

Q. Zhou et al. Locus 042210, Jan. 1, 1998, Accessed Apr. 6, 2001 (see attached computer printout).
R.J. Meis et al. Genetic and molecular biological characterization of a vaccinia virus gene which renders the virus dependent on isatin-beta-thiosemicarbazone (IBT). 1991. Virology, 182:442-454.

* cited by examiner

*Primary Examiner*—Jean C. Witz
(74) *Attorney, Agent, or Firm*—Basil S. Krikelis

(57) ABSTRACT

Disclosed is a composition comprising a substantially purified Cytokine Inhibitory Factor (CIF) having certain characteristics, including the ability to inhibit RNA transcription of the pro-inflammatory cytokines tumor necrosis factor alpha (TNF-$\alpha$), interleukin-1-beta (IL-1$\beta$), and interleukin-2 (IL-2). Also disclosed is a method for substantially purifying the Cytokine Inhibitory Factor and a method for modulating the immune system of an animal using such composition.

34 Claims, 6 Drawing Sheets

Figure 2. Cytokines stimulation *in vitro* by LPS
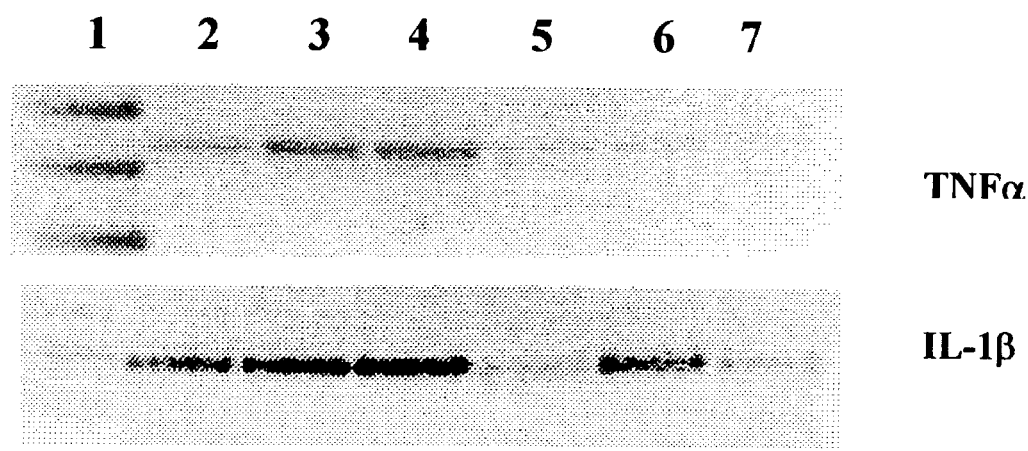
Lane 1.   Standard DNA
Lane 2.   LPS, 5.0 µg/ml
Lane 3.   LPS, 1.0 µg/ml
Lane 4.   LPS, 0.2 µg/ml
Lane 5.   LPS, 0.04 µg/ml
Lane 6.   LPS, 0.008 µg/ml
Lane 7.   Blank control Figure 3. Cytokine inhibition *in vitro* by hyperimmune egg lipids
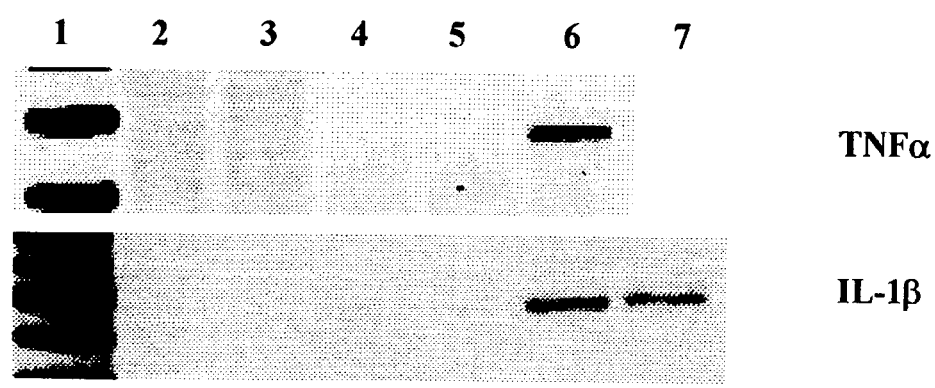
Lane 1.   Standard DNA
Lane 2,3. LPS and EtOH extract of hyperimmune egg lipids, 4 h
Lane 4,5. LPS, 2 h. Washing cells, EtOH extract of hyperimmune egg lipids, 2 h
Lane 6,7. LPS, 2 h. Washing cells, medium 2h

Figure 4. Inhibition of IL-2 *in vitro* by PL-100 egg lipids
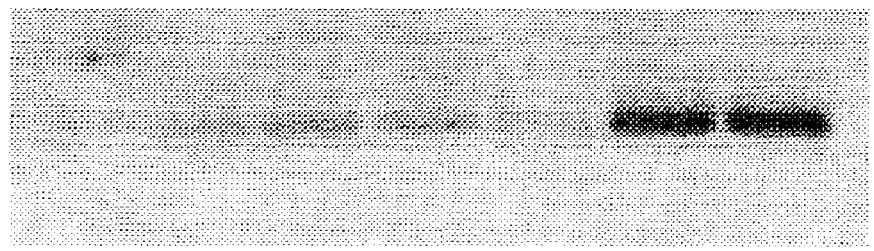
Lane 1.        Standard DNA
Lane 2 & 4.    Acetone extract of PL-100 egg lipids
Lane 3 & 5.    Ethanol extract of PL-100 egg lipids
Lane 6 & 7.    LPS inducing control

Figure 5. Cytokine inhibition in THP$_1$ cells by yolk ethanol extract HPLC fractions
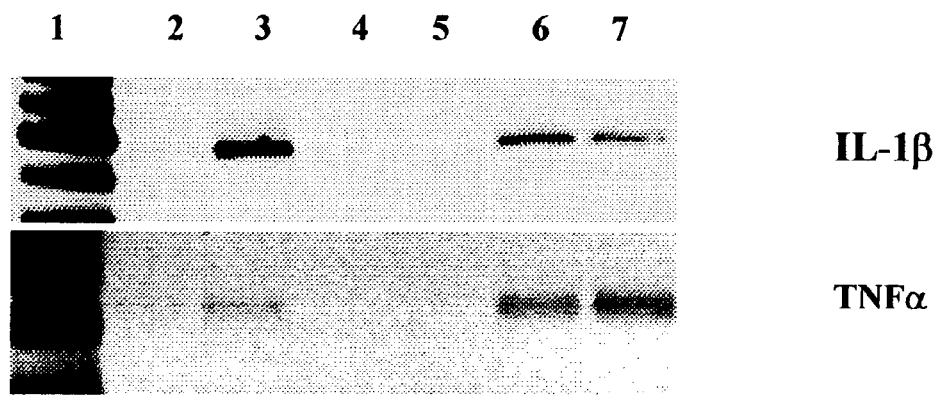
Lane 1. Standard DNA
Lane 2. Blank control – cell alone
Lane 3. CN HPLC fraction 2
Lane 4. CN HPLC fraction 3
Lane 5. CN HPLC fraction 4
Lane 6. CN HPLC fraction 5
Lane 7. LPS control – cytokine induction Figure 6. Inhibition of collagen-induced arthritis by hyperimmune egg yolk
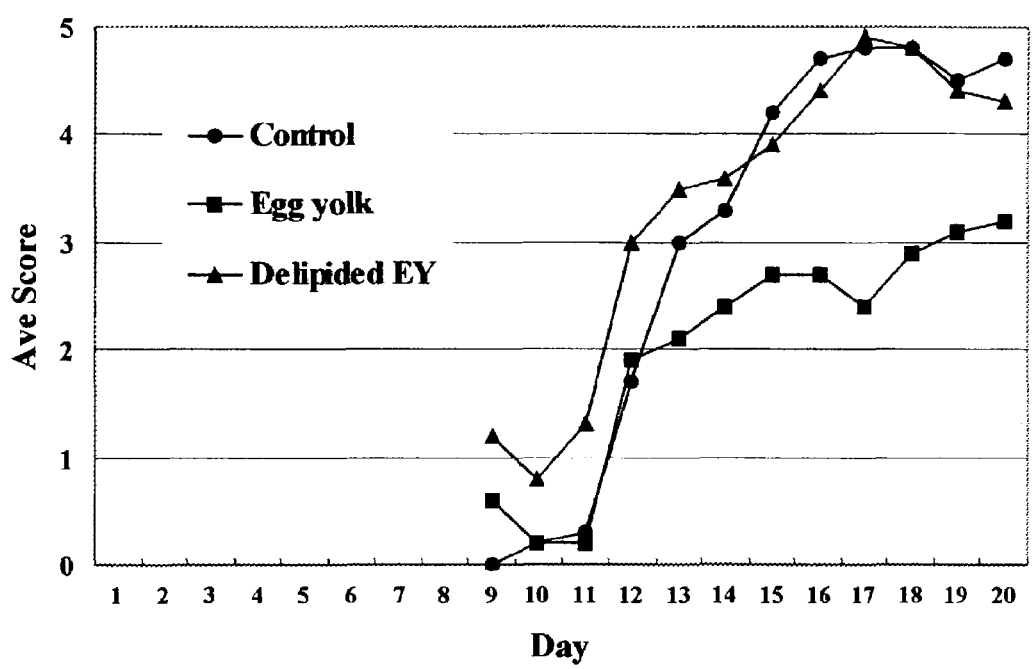

PURIFIED CYTOKINE INHIBITORY FACTOR

CROSS REFERENCE TO RELATED APPLICATIONS

This application claims the benefit of priority under 35 U.S.C. §119(e) from U.S. Provisional Application Ser. No. 60/356,038 filed Feb. 11, 2002, entitled "Highly Purified Cytokine Inhibitory Factor and Methods of Use." The entire disclosure of U.S. Provisional Application Ser. No. 60/356,038 is incorporated herein by reference.

FIELD OF THE INVENTION

The invention generally relates to a biological factor and method for modulating the immune system. The invention specifically relates to a substantially purified cytokine inhibitory factor, methods for its purification, and methods for its use in the modulation of the immune system, particularly directed to reducing inflammation.

BACKGROUND OF THE INVENTION

Biological factors, such as coenzymes, cofactors, vitamins and others, play important roles in biological conversion processes. They are usually produced in small amounts in a whole cell ($1 \times 10^{-5}$–$1 \times 10^{-6}$). Determining the existence of, and thereafter isolating and purifying such biological factors from normal cells, however, is a difficult project.

Hyperimmunized eggs have been developed and have been shown to contain over-produced antibodies and, as set forth in U.S. Pat. No. 6,420,337, certain biological factors. The determination of exactly what biological factors exist in an egg is a difficult one that seems to be made easier with the hyperimmunization process. Hyperimmunization is performed by injection of polyvalent bacterial antigens into the target animal. It has been found that the amount of biological factors found in eggs from these hyperimmunized animals is increased, but by no more than one order of magnitude. Therefore, this small titer of biological factors in hyperimmunized egg makes locating and, thereafter, purification of biological factors difficult. As such, there is a need for an efficient process for recognizing, isolating, purifying or otherwise producing such biological factors.

Cytokines

The normal immune system is under a balance in which proinflammatory and anti-inflammatory cells and molecules are carefully regulated to promote normal host immune defense without the destruction of host's tissues. Once this careful regulatory balance is disturbed, nonspecific stimulation and activation can lead to increased amounts of potent destructive immunological and inflammatory molecules being produced and released. Thus, excess production of proinflammatory cytokines or production of cytokines in the wrong biological context, are associated with mortality and pathology in a wide range of diseases, such as malaria, sepsis, rheumatoid arthritis, inflammatory bowel disease, cancer and AIDS, among others.

Cytokines are pluripotent polypeptides that act in autocrine/paracrine fashions by binding to specific cellular receptors. Their secretion is important in determining the duration and intensity of an immune response. For example, in mice, distinct subsets of CD4+ T helper (Th) clones secrete what have classically been described as Th1 and Th2 cytokines. The cells produce interleukin-2 (IL-2) and interferon-γ (IFN-γ) and facilitate the cellular immune response. Th2 cells produce IL-4, IL-5, IL-6 and IL-10 and support the activation of immunoglobulin secreting cells. During the process of inflammation, cytokines such as IL-1β, IL-2, IL-6 and tumor necrosis factor-α (TNF-α) are released at the site of inflammation. These cytokines have pleiotropic effects and mediate a wide range of symptoms associated with inflammation.

A key cytokine, TNF-α, also known as cachectin, is a 17 kiloDalton protein composed of 157 amino acids and produced mainly by monocytes and activated macrophages. TNF-α has been shown to possess tumoricidal activity as well as a variety of physiological effects with most major organ systems. In the central nervous system, TNF-α is involved in fever, anorexia, and alterations in pituitary hormone release. In the cardiovascular system, TNF-α plays a role in shock, acute respiratory distress and capillary leakage syndrome (procoagulation). TNF-α is instrumental in the process of acute tubular necrosis and nephritis in the kidney and ischemia, colitis, and hepatic necrosis in the gastrointestinal system. It is also a key cytokine involved in the process of inflammation.

Inflammatory conditions are developed by multiple pathogenic processes, in which some key molecules are involved. For example, TNF-α, IL-1β, interlukin-2 (IL-2) and prostaglandin $E_2$ ($PGE_2$) are major contributors in developing inflammation. Inflammation can result in disease states, such as rheumatoid arthritis, septic arthritis, and juvenile osteoarthritis.

TNF-α is produced primarily by T-cells in response to inflammatory stimuli. TNF-α is a potent paracrine endocrine mediator of inflammatory and immune functions, and it modulates endothelial cell functions. For example, TNF-α can be detected in high concentrations in serum and synovial fluid from patients with active rheumatoid arthritis, and is suspected to have a primary role in the pathogenesis of rheumatoid arthritis.

IL-1β is involved in a wide variety of biological pathways, and is a remarkably potent molecule, able to induce its effects by triggering as few as one or two receptors per cell. As a signaling agent, IL-1β is effective at very low concentrations, even in the femtomolar range. IL-1β was first noted for inducing fever, augmenting lymphocyte responses, and stimulating the acute-phase response. The induction of an inflammatory reaction in response to infection is largely attributed to signaling by IL-1β.

Another T-cell-derived cytokine, IL-2, induces growth, differentiation, and functional activation in a variety of cells. For example, IL-2 promotes T-and B-cell growth and differentiation, immunoglobulin secretion by B-cells, NK cell growth and activity, and the production of other cytokines. IL-2 also plays an important function on the numerous inflammatory processes associated with immune cell growth and proliferation.

Prostaglandin $E_2$ ($PGE_2$)

Prostaglandin $E_2$ ($PGE_2$) is a "primary prostaglandin" found throughout many cells in the body. It is the predominate arachidonate metabolite and plays an important role in regulating vascular osmotic potentials as well as general conditions of the organism pertaining to body temperature, pain, immunosuppression, and inflammation. $PGE_2$ is a major constituent in the inflammatory pathway of chronic inflammatory disease states.

A variety of enzymes are responsible for production of $PGE_2$, and several of the same enzymes produce other prostaglandins, thromboxanes, and inflammatory mediators. For example, $PGE_2$ is produced by both constitutively expressed and inducible forms of cyclooxygenase, COX-1, and COX-2, respectively. COX-2 is dramatically up-regulated when cells are exposed to certain mitogens (e.g. LPS) or cytokines (IL-1), providing a connection between cytokine signaling and $PGE_2$ production.

Since TNF-α, IL-1β, IL-2, and $PGE_2$ are the key inflammatory modulators, they play critical roles in the process of inflammation development.

Lipopolysaccharide (LPS) Analogs

A wide range of lipopolysaccharide (LPS) analogs interfere with cytokine expression in vitro and in vivo. For example, solid lipid nanoparticles (SLN) incubated with murine peritoneal macrophages cause a concentration-dependent decrease in IL-6 production. However, TNF-α and IL-12 are not suppressed. The synthetic lipid A analog SDZ MRL 953 protects against endotoxic shock and bacterial infection, as shown by a study in which 20 cancer patients were treated intravenously with escalating doses of SDZ MRL 953 followed by an intravenous application of endotoxin. Pretreatment with the lipid A analog markedly reduced the release of TNF-α, IL-1β, IL-8, IL-6, and G-CSF, suggesting that the pretreatment with SDZ MRL 953 in patients at risk may help to prevent complications of gram-negative sepsis.

LPS induced production of TNF-α can be inhibited in macrophages and in human monocytes and monoblastic U937 cells. A monosaccharidic lipid A analog, DY-9973, inhibits LPS-induced expression of TNF-α and IL-1β mRNA in U937 cells. In contrast, DY-9973 does not inhibit IL-1β-induced TNF-α production in U937 cells. Thus, monosaccharidic lipid A analog such as DY-9973 can inhibit LPS-induced activation of macrophages and reduce the lethal toxicity of LPS. Furthermore, an early endotoxin tolerance is induced by a nontoxic LPS derivative, monophosphoryl lipid A (MPL), against LPS infection.

In addition to lipid analogs, antibodies against LPS function as neutralizers to protect against LPS infection. Monoclonal antibody to lipid A suppresses the ability of lipid A and LPS from various gram-negative bacteria to induce TNF-α (36–67%) and IL-1 (30–98%) in murine peritoneal macrophages. This MAb also inhibited lipid A-induced TNF-α in mice (87%).

LPS analogs also upregulate cytokine expression. A different lipid A analog (DT-5461a) induces TNF-α, IL-1β, IL-6, and GM-CSF in murine macrophage. Furthermore, DT-5461a enhances production of various cytokines in cells through transcriptional enhancement.

Hyperimmunized Eggs

Various genera of the class Aves, such as chickens (gallus domesticus), turkeys, and ducks, produce antibodies in blood and eggs against immunogens that cause avian diseases, as well as against other immunogens. For example, LeBacq-Verheyden et al. (Immunology 27:683 (974)) and Leslie, G. A., et al. (J. Med. 130:1337 (1969)), have quantitatively analyzed immunoglobulins of the chicken. Polson et al. (Immunological Communications 9:495–514 (1980)) immunized hens against several proteins and natural mixtures of proteins, and detected IgY antibodies in the yolks of the eggs. Fertel et al. (Biochemical and Biophysical Research Communications 102:1028:1033 (1981)) immunized hens against prostaglandins and detected antibodies in the egg yolk. Jensenius et al. (Journal of Immunological Methods 46:63–68 (1981)) provide a method of isolating egg yolk IgG for use in immunodiagnostics. Poison et al. (Immunological Communications 9:475–493 (1980)) describe antibodies isolated from the yolk of hens that were immunized with a variety of plant viruses.

U.S. Pat. No. 4,357,272 discloses the isolation of antibodies from the yolks of eggs derived from hyperimmunized hens. The antibody response was elicited by repetitive injections of immunogens derived from plant viruses, human IgG, tetanus antitoxin, snake antivenins, and Serameba.

U.S. Pat. No. 4,550,019 discloses the isolation from egg yolks of antibodies raised in the hen by hyperimmunization with immunogens having a molecular or particle weight of at least 30,000. The immunogens used to hyperimmunize the chickens were selected from among plant viruses, human immunoglobulins, tetanus toxin, and snake venoms.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999 discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

U.S. Pat. No. 6,420,337 discloses a biological factor isolated from the egg of an avian hyperimmunized with an immunogenic mixture. The biological factor has been purified and sequenced and has been determined to activate certain pro-inflammatory cytokines, therefore referred to as a Cytokine Activating Factor.

European Patent Application No. 99967649.7 discloses an anti-inflammatory composition obtained also from the egg of an avian hyperimmunized with an immunogenic mixture. The anti-inflammatory composition has been partially purified from the egg and is shown to be effective in treating and preventing inflammation.

It has been reported that unsaturated fatty acids, such as omega-3 and -6 fatty acids (which can be found naturally in egg yolk), play an important role in the anti-inflammatory process. Recently, many investigators have been focused on the anti-inflammatory effects of omega-3 and -6 fatty acid enriched fish oil. These studies show that indeed omega fatty acids are effective in prevention of arthritis. The studies do not, however, set forth or present any evidence of the effect of omega fatty acids on pro-inflammatory cytokines or cytokines in general.

Some characteristics of omega fatty acids are that they are partially soluble in water, they have a maximum absorbance at 210–230 nm and their melting points are usually very low (−49° C. to 13.4° C.) due to their structure being that of a long-chain fatty acid.

It has not been reported in the literature that egg yolk phospholipids inhibit pro-inflammatory cytokines and/or synthesis of $PGE_2$. Nor has it been reported that egg yolk contains any known lipopolysaccharide analogs (LPS analogs) that can function as competitors to LPS for the inhibition of pro-inflammatory cytokines and synthesis of $PGE_2$.

The key to the present invention lies in the inventors' finding of a novel factor that occurs naturally in egg and has the ability to inhibit pro-inflammatory cytokines as well as synthesis of $PGE_2$.

SUMMARY OF THE INVENTION

The present invention relates to a composition comprising a substantially purified Cytokine Inhibitory Factor, wherein the Cytokine Inhibitory Factor: has molecular weight less than 6,000 Da; is naturally present in a lipid fraction of egg yolk of avian eggs; has a maximum UV absorbance at a wavelength of 205 nm; is a non-proteinatious substance; has a melting point of between about 39° C. to 42° C.; and inhibits RNA transcription of tumor necrosis factor alpha (TNF-α), interleukin-1-beta (IL-1β), and interleukin-2 (IL-2).

The present invention further relates to a purified Cytokine Inhibitory Factor produced by a process comprising: separating a water-insoluble fraction (WIF) from a water-soluble fraction (WSF) of an egg yolk; separating the water-insoluble fraction into a neutral lipid fraction and a polar lipid fraction; purifying the polar lipid fraction into Cytokine Inhibitory Factor fractions by high performance liquid chromatography.

Finally, the present invention relates to a method of modulating the immune system of an animal, comprising administering to the animal a composition comprising a Cytokine Inhibitory Factor.

BRIEF DESCRIPTION OF THE DRAWINGS

FIG. 2 is a digitized image showing the effect of LPS stimulation of TNF-α and IL-β in an in vitro assay.

FIG. 3 is a digitized image showing the effect of hyperimmune egg lipids on the inhibition of LPS stimulated TNF-α and IL-β in an in vitro assay.

FIG. 4 is a digitized image showing the effect acetone extract and ethanol extract from hyperimmune egg lipids on LPS stimulated IL-2 in an in vitro study.

FIG. 5 is a digitized image showing the effect of HPLC purified fractions of ethanol extract from hyperimmune egg lipids on LPS stimulated TNF-α and IL-1β in an in vitro assay.

FIG. 6 shows the effects of hyperimmune egg yolk and delipinidated egg yolk on collagen-induced arthritis in a collagen-induced arthritis rat model study.

DETAILED DESCRIPTION OF THE INVENTION

Figure 1:
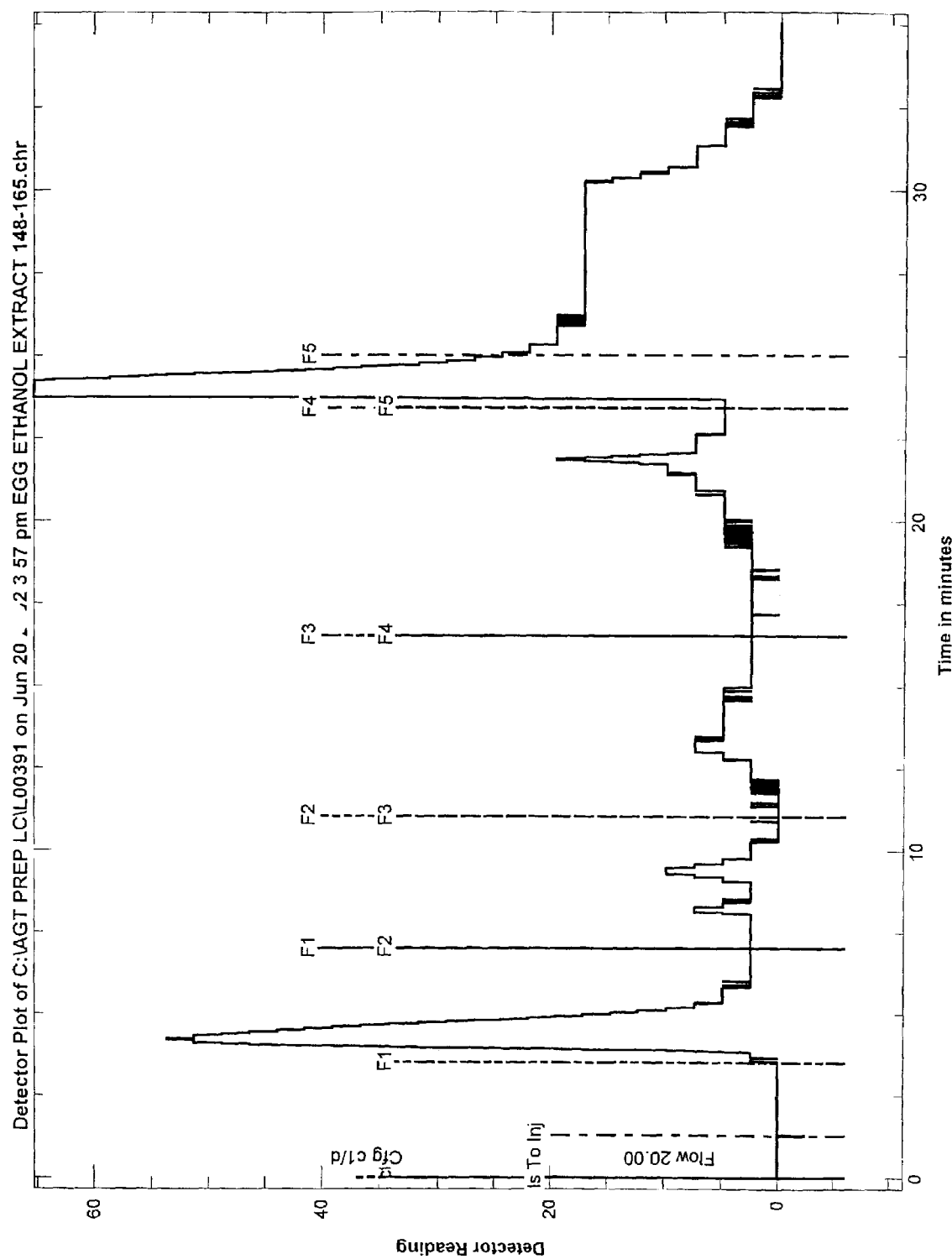
FIG. 1 is an HPLC chromatogram of PL-100 ethanol extract.

The present invention generally relates to a novel Cytokine Inhibitory Factor (CIF), to a composition comprising a Cytokine Inhibitory Factor (CIF), and to a method for modulating the immune system using the composition. The composition of the invention can include compositions comprising purified CIF, and/or a composition of the invention can be a natural food product containing CIF, and preferably, includes a natural food product or fraction thereof which is enriched for the presence of CIF, such as by selection processes or by production of an enriched fraction. Such natural food products include hyperimmune egg products, including fractions of hyperimmune egg products which are enriched for CIF. The present inventors have discovered that the novel CIF, inhibits the expression of tumor necrosis factor-α (TNF-α), interleukin-2 (IL-2) and interleukin-1β (IL-1β), and downregulates the synthesis of prostaglandin $E_2$ ($PGE_2$). Therefore, the CIF of the present invention can be used to modulate (i.e., regulate) the immune system in general by modulating the expression of these cytokines and the cells which produce or are affected by these cytokines. In addition, because TNF-α, IL-1β and IL-2 are typically considered to be proinflammatory cytokines, the CIF of the present invention is useful for the treatment of conditions in which inhibition of an immune response and cells which respond to proinflammatory cytokines is desirable, including, but not limited to, arthritis generally, and, more specifically, rheumatoid arthritis, septic arthritis, and juvenile osteoarthritis. As may be expected, the CIF is also effective in treating and/or preventing most inflammatory conditions or responses as most such conditions or responses involve, at one point or another, TNF-α, IL-1β and/or IL-2.

The CIF of the present invention is a component that is produced and/or enhanced in hyperimmunized egg products. The preferred immunogen mixture that is administered, preferably by injection, to the egg-producing animals to induce an immune response and to produce the hyperimmune egg product that contains Cytokine Inhibitory Factor of the present invention is not required to contain specific immunogens that are known to modulate the immune system by activating particular cytokines or by inducing production of a factor that induces particular cytokines. Therefore, it is surprising to find such a Cytokine Inhibitory Factor in a hyperimmune egg product obtained from animals immunized against a polyvalent vaccine, which is expected to be effective in modulating the immune system when administered to a subject.

Certain characteristics have been determined regarding this novel Cytokine Inhibitory Factor (see Example 3). Initially, the Cytokine Inhibitory Factor (CIF) is located in the lipid portion of the egg yolk of an egg. Therefore, because it is disposed in the lipid fraction, the CIF is non-proteinatious. Through basic knowledge of the lipid portion of an egg, the CIF has been determined to be of a size less than 6000 Daltons. The absorbance of this novel factor has also been studied and it has been determined that the maximum wavelength absorbance of CIF is at 205 nm. The melting point has been found to fall within the range of about 39° C. to 42° C. Finally, as alluded to above, and as described in great detail throughout this application, the CIF inhibits certain cytokines. In particular, the CIF inhibits at least the following pro-inflammatory cytokines: tumor necrosis factor alpha (TNF-α), interleukin-1-beta (IL-1β), and interleukin-2 (IL-2). Finally, the substantially purified CIF of the present invention also inhibits the biosynthesis of prostaglandin $E_2$ ($PGE_2$).

Prior to the present invention, it was not known that hyperimmunization of egg-producing animals would result in the production of the novel Cytokine Inhibitory Factor of the present invention which would have the above characteristics and be capable of regulating cytokine production and the differentiation of cells of the immune system in an animal. To the present inventors' knowledge, prior to the present invention, the Cytokine Inhibitory Factor (CIF) described herein had never been identified, purified, or characterized.

Definitions

The following definitions apply throughout the application unless otherwise specified:

The term "hyperimmunization" means exposure to one or more immunogens (e.g., antigens) such that an immune response is elevated and maintained above the natural unexposed state.

The term "immunogen" means a substance that is able to induce a humoral antibody and/or a cell-mediated immune response rather than immunological tolerance. The term signifies the ability to stimulate an immune response as well as react with the products of it, e.g., antibody.

The term "combinatorial derived immunogens" refers to a process of generating molecular diversity among immunogens by way of combinatorial synthesis.

The term "bioengineered immunogens" refers to immunogens which are obtained through the process of gene cloning technologies and genetic manipulation or chemical synthesis.

The term "genetic vaccine" refers to a nucleic acid vaccine which is generally produced by recombinant technologies and which may elicit an immune response.

The terms "egg" or "egg product" each mean any whole egg (table, hyperimmunized or otherwise) or any product or fraction derived therefrom.

The terms "table egg" or "table egg product" each mean a whole egg, or any product or fraction derived therefrom, obtained from egg-producing animals which are not maintained in a hyperimmune state.

The terms "hyperimmune egg" or "hyperimmune egg product" each mean whole egg or any product or fraction derived therefrom, obtained from an egg The term "Cytokine Inhibitory Factor" or "CIF" is used generally to refer to the biological factor of the present invention at any stage of purity (e.g., including as a component of egg, as a substantially purified lipid fraction of an egg, or as a highly purified lipid fraction of an egg) and having the biochemical, physical, structural and/or functional characteristics (e.g., biological activity) described herein for Cytokine Inhibitory Factor.

The term "Substantially Purified Cytokine Inhibitory Factor" means a Cytokine Inhibitory Factor that has been purified to at least the level set forth in Example 2.

The term "supranormal levels" means levels in excess of those found in eggs of egg-producing animals not maintained in a hyperimmune state.

The terms "immunoregulatory egg" or "immunoregulatory egg product" mean egg or egg fractions containing the Cytokine Activating Factor disclosed herein.

The term "immune response" refers generally to a cell-mediated or cellular immune response (i.e., an immune response mediated by cells of the immune system including T lymphocytes, B lymphocytes and macrophages) and/or a humoral immune response (i.e., an immune response mediated by antibodies).

The term "animal" refers to any species of the kingdom, Animalia. Preferred animals to immunize according to the present invention include any animals of the Vertebrate class, Aves, including, without limitation, chickens, turkeys, and ducks. Preferred animals to treat according to the present invention include any animals of the Vertebrate classes, Aves and Mammalia, including, without limitation, primates, rodents, livestock and domestic pets. Livestock include mammals to be consumed or that produce useful products (e.g., sheep for wool production). Preferred mammals to protect from a disease or condition include humans, dogs, cats, mice, rats, sheep, cattle, horses and pigs, with humans being particularly preferred.

The term "target animal" refers to an animal that is administered the immunogenic mixture.

The term "subject animal" refers to the animal which is administered a CIF-containing composition of the present invention, including compositions containing purified CIF, or a CIF-enriched egg or egg product produced by the target animal. A subject animal can also be referenced as a patient.

The phrase "biologically active" or "biological activity" with reference to a CIF of the present invention refers to any functional activity of a CIF, and typically, a functional activity of a naturally occurring CIF. In particular, reference to the biological activity of a CIF preferably refers to the ability of a CIF to downregulate (inhibit, reduce, decrease, suppress) the expression of a cytokine which includes tumor necrosis factor-α (TNF-α), interleukin-1β (IL-1β), and/or interleukin-2 (IL-2). It is noted that naturally occurring CIF as described in detail herein can downregulate the expression of each of TNF-α, IL-1β and IL-2. CIF biological activity can also include an ability to downregulate (inhibit, decrease, suppress) the expression of prostaglandin $E_2$. A biological activity of CIF can also include, but is not limited to an ability of CIF to bind to a receptor, a protein, DNA, a carbohydrate moiety or a lipid moiety, which results in or contributes to one of the above-identified biological activities.

The term "maximum wavelength absorption" refers to the absorption of electromagnetic radiation in the UV and visible regions of a compound that reflects different abilities to individual wavelengths. The absorption of radiation is caused by subtraction of energy from the radiation beam when electrons in orbitals of lower energy are excited into orbitals of higher energy. The absorption depends on the wavelength of the radiation and the structure of the compound. The highest absorbed wavelength is the maximum wavelength absorption of the tested compound.

The term "modulate" or derivatives of such term, means to change, regulate or vary from one state to another, and includes a measurable or observable increase or decrease in any measurable characteristic and/or a change from one characteristic to another, different characteristic.

The phrase "pharmaceutically acceptable carrier" refers to pharmaceutically acceptable excipients, formulations and/or pharmaceutically acceptable delivery vehicles, which are suitable for use in administration of a composition of the present invention to a suitable in vitro, ex vivo or in vivo site. Pharmaceutically acceptable carriers can enable compositions of the present invention to be produced/provided in any suitable form for use, including, but not limited to, a liquid, an aerosol, a capsule, a tablet, a pill, a powder, a gel and a granule. Some pharmaceutically acceptable carriers include cells, membranes, lipid formulations (including liquids that, upon administration to a patient, form a solid or a gel in situ), antibody formulations, food products (e.g., any edible product or preparation) and recombinant viruses. Preferred carriers are also biodegradable (i.e., bioerodible).

A "pharmaceutically acceptable excipient" includes excipients or formulations that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzyl alcohol.

A "controlled release vehicle" is a type of pharmaceutically acceptable carrier that is capable of releasing a composition of the present invention in a controlled manner into a patient or culture. A controlled release formulation comprises a compound of the present invention (e.g., a CIF composition, an antibody, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems.

A "pharmaceutically acceptable delivery vehicle" is a pharmaceutically acceptable carrier which is capable of delivering a composition of the present invention to a target site. Preferably, pharmaceutically acceptable delivery vehicle is capable of targeting (i.e., directing, selectively delivering) the composition to the target site. A "target site" refers to a site in a patient to which one desires to deliver a composition. For example, a target site can be any cell or tissue which is targeted by direct injection or delivery using artificial and natural lipid-containing delivery vehicles (e.g., liposomes), antibodies, viral vectors or other delivery vehicles, including ribozymes. Natural lipid-containing delivery vehicles include cells and cellular membranes. Artificial lipid-containing delivery vehicles include liposomes and micelles.

The term "administer" means any method of providing a subject with a substance (e.g., introducing a substance into a subject), including by in vivo or ex vivo administration. Methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, intraocular, pulmonary administration, impregnation of a catheter, by suppository and direct injection into a tissue.

The term "therapeutic benefit" does not necessarily refer to a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition.

The term "protection" with reference to a disease or condition refers to reducing the symptoms of the disease; reducing the occurrence of the disease, and/or reducing the severity of the disease. Protecting a patient or subject can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment).

The term "prevention" means that the progression of the disease is reduced and/or eliminated, or that the onset of the disease is eliminated (prophylactic treatment).

The term "treatment" means that the onset of the symptoms (including pain) of the disorder and/or pathogenic origin of the disorder be delayed, reduced, or completely prevented, or, if present, the symptoms be ameliorated or completely eliminated. For example, the CIF composition treats arthritis not only by suppressing the symptoms of the disorder in humans and other mammals, but also by acting as a prophylactic agent to counteract the presence of the disorder in the recipient.

The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

The term "a" or "an" entity refers to one or more of that entity. As such, the terms "a" (or "an"), "one or more" and "at least one" can be used interchangeably herein.

The terms "comprising", "including", and "having" can be used interchangeably.

Hyperimmunization

While it is preferred that the composition of the present invention be purified from hyperimmune eggs it is also contemplated that the Cytokine Inhibitory Factor can be purified from table egg. A detailed description of a preferred procedure used to bring an egg-producing animal to a heightened state of immunity from which the resultant hyperimmune egg or egg product can be administered to a subject is disclosed in U.S. Pat. No. 5,772,999, incorporated herein by reference in its entirety. Briefly, the following is an example of the procedure used to bring an egg-producing animal to a heightened state of immunity for use in purification of CIF or for production of a CIF-enriched food product for administration to a subject. It is to be understood that such a procedure can be modified as discussed above to select or screen for enhanced CIF production. In general, the hyperimmunization process includes the steps of:

1. Selecting one or more antigens.
2. Eliciting an immune response in the egg-producing animal by primary immunization.
3. Administering booster vaccines of antigens of appropriate dosage to induce and maintain the hyperimmune state.
4. Collecting and processing the eggs to produce a hyperimmune egg product from the egg-producing animal maintained in the hyperimmune state.

Step 1 Any antigen or combination of antigens may be employed. The antigens can be bacterial, viral, protozoan, fungal, cellular, or any other substances to which the immune system of an egg-producing animal will respond. The critical point in this step is that the antigen(s) must be capable of inducing immune and hyperimmune states in the egg-producing animal. One preferred vaccine is a mixture of polyvalent bacterial antigens, referred to as PL-100 vaccine. The bacteria included in the PL-100 vaccine are listed in Table 1 of U.S. Pat. No. 5,772,999.

Step 2 The vaccine can be either a killed or live-attenuated vaccine and can be administered by any method that elicits an immune response. It is preferred that immunization be accomplished by administering the antigens through intramuscular injection. The preferred muscle for injection in an avian is the breast muscle. Dosage is preferably 0.5–5 milligrams of the antigen(s) vaccine. Other methods of administration that can be used include intravenous injection, intraperitoneal injection, rectal suppository, or oral administration. When DNA techniques are used for the hyperimmunization process, much smaller quantities are required, generally 1–100 micrograms. It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. In general, the appearance of egg antibodies after immunization with the vaccine is indicative of an immune response. The minimum dosage of antigen necessary to induce an immune response depends on the vaccination procedure used, including the type of antigen(s) used as well as the type of egg-producing animal used as the host.

Step 3 The hyperimmune state is preferably induced and maintained by repeated booster administrations of an appropriate dosage at fixed time intervals. The time intervals are preferably two-week intervals over a period of six months. However, it is essential that the booster administrations do not lead to immune tolerance. It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

Step 4 The hyperimmune eggs can be processed for administration to the subject or for purification in a variety of ways. These include preparation of a composition comprising the hyperimmune egg product substantially by itself (e.g., in capsules) and incorporation of the hyperimmune egg product into foods for administration to a subject, or following the purification protocol for Cytokine Inhibitory Factor as described elsewhere herein.

Purification of Cytokine Inhibitory Factor

The Cytokine Inhibitory Factor of the present invention can be separated and substantially purified from egg using solvent extraction and normal-phase HPLC technologies (See Examples 1 and 2). In vitro cytokine expression studies, and bio-assay data have all demonstrated the purification of a biologically active Cytokine Inhibitory Factor.

Preferably, the yolk lipids are extracted from hyperimmune egg using solvent extraction. A phospholipid fraction is then separated from a neutral lipid fraction through selective solvent extraction methods. The phospholipid fraction contains multiple immune modulators, and inhibits pro-inflamatory molecules, such as TNF-α, IL-1β, IL-2 and $PGE_2$ in vitro.

The Cytokine Inhibitory Factor of the present invention is disposed within the phospholipid fraction of hyperimumme egg yolk. This phospholipid fraction suppresses cytokine mRNA, as shown by comparative analysis of mRNA transcription in cells that have been treated with the cytokine stimulant lipopolysaccharides (LPS), and this activity is attributed to the action of the Cytokine Inhibitory Factor.

Monocytes produce minimal TNFα and IL-1β under normal growth conditions. However, the expression of cellular cytokine mRNA is induced to higher levels by treatment with LPS. As presented in the Examples below, cells were stimulated by LPS to enhance cytokine expression. The enhanced cytokine expression was then suppressed by the hyperimmune yolk phospholipid fraction. Additional LPS was removed from the cells, and as a result, mRNA of TNFα and IL-1β were purged from the cell by the yolk phospholipid fraction. Therefore, this phospholipid fraction comprises at least one Cytokine Inhibitory Factor. The results presented below demonstrate that the yolk phospholipid fraction does not react with LPS and it's effect neutralizes LPS induction for cytokine expression. The yolk phospholipid fraction inhibits the transcription of cytokine mRNA specifically.

As specifically set forth in the examples below, four pro-inflammatory modulators, TNF-α, IL-1β, IL-2, and $PGE_2$ were examined via LPS induction of the pro-inflammatory modulators in monocytes (human and mouse). The expression of cytokines at mRNA level as well as $PGE_2$ production at protein level was measured. The yolk phospohlipid fraction inhibited the expression of TNF-α, IL-1β, IL-2 and $PGE_2$.

Extraction of Yolk Phospholipid Fraction

Preferably, the Cytokine Inhibitory Factor of the present invention is substantially purified from either whole egg, egg yolk or a lipid fraction of egg yolk from a hyperimmunized avian. In the purification process, the egg yolk is eventually subjected to solvent extraction. Solvent extraction can be applied to the egg yolk itself or any other form of the yolk, such as, for example, spray-dried egg yolk. Different solvents may be used for this purpose. Non-polar solvents, such as hexane, are useful to remove neutral lipids in the yolk, or lipid fraction of the yolk. Subsequently, polar solvents, such as methanol and ethanol, are useful to extract a phospholipid fraction. Alternatively, several solvents are appropriate for the various extraction procedures, such as acetone and chloroform. A variety of solvents may be selected for the purification application depending on the requirements and optimization of the process, scale-up, and applicable regulations.

Another avenue for isolation and purification of the Cytokine Inhibitory Factor of the present invention is through supercritical fluid extraction (SFE). SFE removes the neutral lipid fraction, containing neutral lipids such as triglycerides and cholesterol, from yolk lipids. The neutral lipids comprise approximately 70% of the total yolk lipids. For example, supercritical carbon dioxide extraction may be an effective procedure for removing most of the cholesterol and fat from egg yolk without damaging functionality of the phospholipid fraction. Phospholipids are not removed during SFE by carbon dioxide, and the carbon dioxide may be beneficial in maintaining emulsification properties. Phospholipids, however, can be extracted by other solvents such as propane.

Administration

In other embodiments, the composition of the present invention can include CIF in purified, recombinant, chemically synthesized, substantially purified, or any other enriched form. For purposes of administration, the CIF, in any suitable form, can be administered in combination with any suitable pharmaceutically acceptable carrier. Suitable pharmaceutically acceptable carriers according to the present invention include pharmaceutically acceptable excipients, controlled release vehicles, and pharmaceutically acceptable delivery vehicles as described above. The composition can be in any form suitable for delivery, including, but not limited to, a liquid, an aerosol, a capsule, a tablet, a pill, a powder, a gel and a granule. Preparations of the CIF that are particularly suitable for parenteral administration include sterile aqueous or nonaqueous solutions, suspensions or emulsions. Examples of nonaqueous solvents or vehicles are propylene glycol, polyethylene glycol, vegetable oils such as olive oil and injectable organic esters such as ethyl oleate.

In solid dosage forms, the CIF protein can be admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents, pH-sensitive polymers, or any other slow-releasing encapsulants (i.e., controlled release vehicles) which are typically used as encapsulating compositions in the food and drug industry or any other controlled release formulations. Tablets and pills can additionally be prepared with an enteric coating.

Liquid dosage forms of the Cytokine Inhibitory Factor for oral administration include pharmaceutically acceptable emulsions, solutions, suspensions, syrups and elixirs, containing inert diluents commonly used in the pharmaceutical art. Besides inert diluents, compositions can also include wetting agents, emulsifying, and suspending, and sweetening agents.

In one embodiment, the composition is in the form of a food product. In this embodiment, in one aspect, the immunoregulatory egg or any CIF-enriched fraction thereof is integrated into a nutritional supplement. One preferred method for preparing the egg, or any fraction thereof, to be incorporated into a nutritional supplement involves drying the egg into a powder. Although various methods are known for drying eggs, spray drying is a preferred method. The process of spray drying eggs is well known in the art. Such a dried egg powder can be ingested as just plain egg powder, or can be incorporated into drinks in the form of, for example, protein powders, power building drinks, protein supplements and any other nutritional, athlete-associated products. In addition, the egg powder can be used in bake mixes, power bars, candies, cookies, etc. Other examples of egg processing include making an omelet, soft or hard-boiling the egg, baking the egg, or, if desired, the egg can be eaten raw or processed as liquid egg. Preferred fractions of the immunoregulatory egg product of the present invention include, but are not limited to: liquid egg yolk, powdered egg yolk, and/or a lipid fraction of said hyperimmunized egg product.

A composition of the present invention can be delivered (i.e., administered) to a cell culture (such as in a cytokine assay) or patient by any suitable method. Selection of such a method will vary with the type of compound being administered or delivered (i.e., purified fraction, protein, nucleic acid, mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in regulation of an immune response in a subject. Preferably, the composition of the present invention is administered to a subject animal by any means that modulates the immune system in the subject animal.

Administration routes include in vivo, in vitro and ex vivo routes. In vivo routes include, but are not limited to, oral, nasal, intratracheal injection, inhaled, transdermal, rectal, impregnation of a catheter, by suppository, direct injection into a tissue, and parenteral routes. Preferred parenteral routes can include, but are not limited to, subcutaneous, intradermal, intravenous, intramuscular and intraperitoneal routes. In one embodiment of the present invention, a composition containing a CIF fraction, protein, antibody, mimetic, or nucleic acid molecule of the present invention is administered by a parenteral route. Intravenous, intraperitoneal, intradermal, subcutaneous and intramuscular administrations can be performed using methods standard in the art. Aerosol (inhalation) delivery can also be performed using methods standard in the art (see, for example, Stribling et al., Proc. Natl. Acad. Sci. USA 189:11277–11281, 1992, which is incorporated herein by reference in its entirety). In another embodiment, a composition comprising a CIF fraction of the present invention is administered orally. Oral delivery can be performed by complexing a therapeutic composition of the present invention to a carrier capable of withstanding degradation by digestive enzymes in the gut of an animal. It is noted that a CIF fraction of the present invention is particularly resistant to digestive enzymes, and therefore, such a carrier may not be critical. Examples of such carriers, include plastic capsules or tablets, such as those known in the art. Such routes can include the use of pharmaceutically acceptable carriers as described above. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell.

In one embodiment, immunoregulatory eggs or fractions thereof, of the present invention, are processed to produce a hyperimmune egg product which can subsequently be administered to a subject animal. In one embodiment, administration occurs by directly feeding the egg, or any derivative thereof to the subject animal. It is important to note that egg is a natural food ingredient that is non-toxic and safe. Similarly, in another embodiment, it is preferred that the substantially purified Cytokine Inhibitory Factor be prepared (e.g., formulated) in a manner which can subsequently be administered to an animal.

When it comes to modulation of the immune system, the composition of the present invention is preferably administered to the subject in an amount that is immunologically effective in inhibiting cytokine (i.e., TNF-$\alpha$, IL-1$\beta$, IL-2 and/or $PGE_2$) expression and preferably, cytokine inhibition and immune modulation. Duration and intensity of the treatment will depend upon the particular subject and condition, of the subject and whether it is present, and, if so, the advancement of the condition in the subject. The composition is also provided in any amount that treats and/or prevents the condition and the symptoms of the condition.

For example, in the case of administration of immunoregulatory eggs or products produced therefrom, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods described herein as well as other known methods in the art. With regard to administration to a subject of the immunoregulatory egg or egg product, it has been determined that the preferred dose range of hyperimmune egg or egg product to be given to a subject is between 100 milligrams to 10 grams per kilogram of subject weight.

With regard to the isolated Cytokine Inhibitory Factor of the present invention, including substantially purified CIF, recombinant CIF and/or chemically synthesized CIF, it has been determined that the preferred dose range of the substantially purified composition is between 1 nanogram and 400 milligrams per kilogram of the subject weight. In a preferred embodiment, the preferred dose range is between about 0.01 microgram and about 100 milligrams per kilogram of the subject weight. In another embodiment, a protein or antibody is administered in an amount that is between about 0.1: g and about 10 mg per kg body weight of the patient, and more preferably, between about 0.1: g and about 100: g per kg body weight of the patient.

It will be obvious to one of skill in the art that the number of doses administered to a patient is dependent upon the goal of the administration (e.g., the extent of the inflammatory condition and the response of an individual patient to the treatment). Therefore, it is within the scope of the present invention that a suitable number of doses includes any number required to regulate an immune response in an animal, or to regulate a disease or condition which is expected to be treated or prevented by downregulation of proinflammatory cytokines (TNF-α, IL-1β, IL-2) and/or by downregulation of $PGE_2$. Effective in vivo dose parameters can be determined using methods standard in the art. Such methods include, for example, determination of survival rates, side effects (i.e., toxicity), determination of cellular and humoral immune response effects, and/or effects on conditions related to such immune response effects.

It is one embodiment of the present invention to provide a method for modulating an immune response in an animal. This embodiment includes the steps of administering to an animal a composition as previously described herein, comprising a substantially purified Cytokine Inhibitory Factor of the present invention. In a preferred embodiment, the composition comprises a pharmaceutically acceptable carrier, also previously described herein. In this embodiment, the composition of the present invention can be used as a local or systemic stimulator of the immune system. It could also prevent and/or treat localized and systemic bacterial infection and could be employed as a general anticancer agent. It could also be tagged with specific delivery reagents like tissue specific antibodies, so as to deliver through the intravenous route to the specific site of bacterial infection or tumor formation. It could also be mixed with specific liposomes or delivery vehicles that are available commercially, so as to deliver it through the cytoplasmic and nuclear membrane of the cell and thereby facilitating the inhibition of TNF-α, IL-1β, and/or IL-6 expression at the RNA level. Suitable modes of administration, including preferred routes and doses, are described above. Preferably, an animal is administered a composition of the present invention in a dose and by a route suitable to regulate an immune response by increasing the expression of TNF-α, IL-1β, IL-2 and/or $PGE_2$.

The advantageous properties of this invention can be observed by reference to the following examples which illustrate the invention. These examples are provided for the purposes of illustration and are not intended to limit the scope of the present invention.

EXAMPLES

Example 1

Fractionation of PL-100 Yolk Lipids

PL-100 eggs were delipidated using a buffer that was prepared by dissolving glacial acetic acid (0.44 ml), sodium acetate (3.06 g) and sodium chloride (5.26 g) in 1,300 ml ultrapure water. The buffer had a pH value of approximately 5.0. Egg material (100 g spray-dried egg or 200 ml shell egg) was added to the buffer and the egg mixture was further homogenized by blending at room temperature for 5 minutes at 24,000 rpm. The homogenized egg mixture was stirred at 4° C. for 4 hours to allow maximum solubility. Caprylic acid (15 ml) was added to the egg mixture and homogenized by blending at room temperature for 3 minutes at 24,000 rpm. The egg mixture then stayed at room temperature for 2 hours, allowing for phase-separation. Flocculate and foams were then mixed with the aqueous phase and centrifuged at room temperature for 10 minutes at 2,190×g. The supernate was filtered using 40 micron porosity filter paper, and the filtrate was lyophilized to dryness. The pellet, which contained lipids and water-insoluble proteins, was collected for further lipids extraction. This fraction is referred to as the Water Insoluble Fraction (WIF).

Egg lipids may be extracted from either the Water Insoluble Fraction (WIF) from the above acidic extraction procedure, or from liquid egg yolk as the source material. For solvent extraction of the egg lipids, 800 Grams of either egg liquid yolk or the WIF pellet was mixed with 1,000 ml acetone in a sealed bottle. The neutral lipids, such as triglycerides and cholesterol, were extracted by acetone three times, for 3 minutes, by violent mixing or blending at 24,000 rpm. The acetone extract was filtered through 40 micron Whatman fold filter paper. Residues of particles undissolved in acetone/the residue from the filter paper of the acetone extraction were further mixed in 1,000 ml methanol and the polar lipids and Cytokine Inhibitory Factor was extracted three times at 3 minutes each. Methanol was removed by evaporation using a rotary evaporator under a reduced pressure of 5 pounds per square inch (PSI) at 50° C. Trace amounts of methanol and water in the extract were removed by lyophilization. The dried methanol extract was stored at −20° C., as a yellow paste. For future use, the methanol extract fraction can be dissolved in methanol, ethanol, methylene chloride, and chloroform and partially dissolved in water. Alternatively, ethanol can be used in place of methanol in the extraction of egg lipids according to the above procedure.

The components of the egg can be separated based on solubility in various solvents. Egg yolk contains approximately 62% lipid and 30% protein. Of the lipid portion, the neutral lipids, which are mostly triglycerols, are a significant portion of the total lipids, comprising approximately 65% of the total lipids. The neutral lipids are non-polar and highly soluble in hydrocarbon solvents, such as hexane or benzene. They are however quite insoluble in more polar solvents.

Conversely, the phospholipids comprise about 30% of the total lipids, or 18% in total yolk mass. Phospholipids are quite polar as a result of the choline or ethanolamine molecule esterified to phosphoric acid, and are therefore easily extracted by polar solvents, such as methanol and ethanol.

The yield of phospholipid extract in both liquid yolk and dried yolk powder was about 10% in yolk mass by the solvent extraction (See Table 1). Some phospholipids were extracted and discarded during the acetone extraction process as acetone has a moderate polarity, and it can extract a portion of phospholipids with the neutral lipids. The yield of phospholipids may be increased by using non-polar solvents, such as hexane, to extract the neutral lipids.

TABLE 1

| Methanol extraction of egg phospholipids | |
|---|---|
| Egg yolk[1] | Yield (%) of phospholids[2] |
| PL-100 Spray-dried whole egg | 3.3 |
| PL-100 Spray-dried egg yolk | 8.0 |

TABLE 1-continued

Methanol extraction of egg phospholipids

| Egg yolk[1] | Yield (%) of phospholids[2] |
|---|---|
| SPAFAS[3] Spray-dried egg yolk | 10.4 |
| PL-100 Shell whole egg | 4.8 |
| PL-100 Sheel egg yolk | 12.4 |

[1]Whole egg and egg yolk contain 34% and 51% dried mass, respectively.
[2]Yields of methanol extract of shell egg were calculated with dry mass in total sheel egg.
[3]SPAFAS egg is non-immune egg.

Example 2

HPLC Purification

The polar or phospholipid extract from the extraction procedure described in Example 1, may be further purified into CIF fractions using normal phase HPLC. The HPLC chromatogram (see FIG. 1) showed five fractions from the phosopholipid fraction. Of the five fractions, two fractions were especially effective at inhibiting TNF-α and IL-1β expression in vitro.

The HPLC separation was performed on a normal phase HPLC column (25×2.12 cm Zorbax PRO1/150 CN) on an Americhrome HPLC system. Four solvents were used for the separation: Solvent A was 99.50% heptane in 0.05% ethanol; Solvent B was 94% heptane in 6% ethanol; Solvent C was 90% heptane in 10% ethanol; and Solvent D was 1000% ethanol.

For the separation, approximately 4.0–4.5 grams of the phospholipid extract was dissolved in 150 ml of Solvent A, and filtered through a 0.2 μm porosity membrane to remove an undissolved materials. A clear yellow solution was obtained.

The clear yellow solution was then separated using HPLC. The step gradient on the column was Solvent A (0–2 minutes), Solvent B (2.01–18.0 minutes), Solvent C (18.01–30.0 minutes), Solvent D (30.01–40.0 minutes), and Solvent A (40.01–60.0 minutes). From this, five fractions were collected, as shown in FIG. 1. The detection wavelength was 254 nm, and fractions 1 (F1) and 5 (F5) showed the highest detection reading. The HPLC separation was conducted over many injections, and the fraction pools were collected. The solvents were removed by evaporation using a rotovap.

The HPLC separation described increased the purity of Cytokine Inhibitory Factors (CIF). Each of the fractions had a yellow color of varying intensity. As the chromatogram in FIG. 1 shows, most of the materials in the phospholipid fraction were separated into fractions 1 (F1) and 5 (F5), whereas fractions 2–4 (F2, F3, and F4) were more highly purified materials.

Example 3

Characterization of Cytokine Inhibitory Factor

The Cytokine Inhibitory Factor (CIF), substantially purified to the level set forth in Example 2 above, was further characterized to determine specific characteristics. Briefly, the following basic studies were run and associated characteristics were determined.

The maximum wavelength of the substantially purified Cytokine Inhibitory Factor was measured by a spectrophotometer equipped on Shimadzu HPLC diode array detector, and was determined to be 205 nm.

The melting point of the substantially purified Cytokine Inhibitory Factor (CIF) was measured by visional observation by putting cold CIF in an increasing warm water bath, and was determined to be within the range of 39° C.–42° C.

The molecular weight of the substantially purified CIF was estimated as current study data. It is known in the art that most of the compounds in the phospholipid fraction of egg yolk are small molecules (200–6,000 Dalton).

The solubility of the substantially purified CIF fraction was measured by adding 100 mg CIF in 1.0 ml solvent at room temperature. The solubility was checked by visional observation.

It was finally determined that the CIF can not be a protein because proteins are not soluble in methanol, ethanol, and/or chloroform.

Example 4

IN vitro Cytokine Inhibition

Cytokine inhibition assay was performed with incubation of human monocyte, THP1, following by RT-PCR procedure to measure the expression of cytokine mRNA. The entire assay included four steps: cytokine inhibition, RNA extraction, cDNA synthesis, and PCR reaction.

Cytokine inhibition in vitro: For cytokine inhibition assay, THP1 cells at a concentration of ~1×105 cells were incubated in 10 mL RPMI 1640 medium with LPS (mostly 0.2 μg/ml) to induce cytokines in cells. The cells were also incubated with yolk lipid fractions (5 μg/ml) simultaneously for 4 hrs at 37° C. Cells were harvested and mixed with 750 ml of Trizol (GIBCO BRL).

RNA Extraction: After incubating the cell mixture for 10 min at room temperature, 250 μl of chloroform was added and the mixture was vigorously shaken by hand for a further 20 sec. The mixture was left at room temperature for 10 minutes and centrifuged at 12,000×g for 5 min. The top clear aqueous layer was removed carefully into a fresh microcentrifuge tube, and 500 μl of isopropyl alcohol was added. The RNA mixture was centrifuged at 12,000×g at room temperature after incubating for 10 min at room temperature. Pellet containing RNA was washed with 1.0 ml of cold 70% ethyl alcohol and then centrifuged at 12,000×g for 5 minutes at room temperature. RNA was dissolved in 40 μl of sterile distilled water (RNase free), mixed by vortex gently, and incubated at 65° C. with the lids open to evaporate off the remaining 70% ethanol. The quality of RNA was checked by loading 1.0 μl on a 1% agarose gel in 1×TBE running buffer with a λ DNA digested with Hind III enzyme as standard RNA. Finally, RNA was stained using 10 μl Gold nucleic Acid Gel Stain (Molecular Probes) in 100 mL 1×TBE buffer for 20 min and the gel was visualized under UV.

cDNA synthesis: 10 μl of the RNA sample and 1.0 μl of Oligo dT Primer were added in a PCR tube. RNA was incubated at 65° C. for 10 min, followed by 2 min incubation at room temperature in a PCR machine. PCR tubes were centrifuged to spin the samples down to the bottom and 8 μl of the master mix was added to the tube. The master mix contained 1.0 μl of RNase Inhibitor, 4 μl of 5×RT buffer, 1.0 μl 100 mM dNTPs, 1.0 μl 80 mM sodium pyrophosphate, and 1.0 μl AMV Reverse Transcriptase. The tubes were incubated in a PCR machine at 42° C. for 1 hr, followed by a 2 min incubation at 95° C. After spinning the tubes briefly, 1.0 μl of 0.5 M EDTA, pH 8.0 and 20 μl of phenol-chloroform were added, and the samples were mixed by vortex then spun for 2–3 minutes. The top aqueous layer was removed into a new tube (~18 ul), and 20 µl of ammonium acetate and 125 µl isopropanol were added. The sample was stirred by vortex for 10 seconds and incubated in dry ice/ethanol slush (−20° C.) for 1 hr. By spinning the tubes at 12,000×g for 10 min at room temperature, the supernatant was discarded and the pellet was washed with 1 ml of 70% ethyl alcohol. RNA mixture was span at 12,000×g for 5 min at room temperature, and the ethanol was removed.

PCR reaction: GAPDH primer was initially employed to make sure cDNA levels are equal in all samples. 100 µl PCR reaction mixture contained 10×PCR buffer (Gibco BRL, no MgCl2), 2.5 µM dNTP (Gibco BRL), 3.0 µl MgCl2, 2.0 ml primer set for each cytokine, 1.0 µl Taq DNA Polymerase, and 63 µl sterile PCR water (Gibco BRL). 1.0 µl of cDNA and 4.0 µl of sterile distilled water were added in each PCR tube. PCR reaction was set as standard procedure.

Once the PCR was finished, 50 µl of chloroform was added to each tube. Vortex with the lids tightly shut and centrifuge at 12,000×g for 1 min. The upper aqueous layer was transferred into fresh labeled tubes. Thereafter, 15 µl of each sample was applied in 1.5% agarose gel in 1×TBE running buffer, and cytokine DNA was run on the gel with 100 bp standard ladder as control. Gel was stained using 10 µl Gold Nucleic Acid Gel Stain (Molecular Probes) in 100 ml 1×TBE buffer for 20 min and viewed under UV detector.

Result

LPS stimulates human monocytes to produce TNFa and IL-1b (6). This result is constant to our study. LPS induced THP1 cells to express both of the cytokines (FIG. 2). The maximum induction for TNFa was at around 0.2 mg/ml medium. High concentration of LPS showed poor induction as well as the low concentration in culture medium. LPS was able to induce IL-1b at very low concentration (0.008 mg/ml), indicating that IL-1b was a more sensitive cytokine to respond LPS induction.

By using the LPS induction assay, it was determined that the expressions of TNFa, IL-1b, and IL-2 in the human monocytes were inhibited by yolk phospholipid fraction. Cellular TNFa and IL-1b showed complete inhibition when the cells were incubated with 0.2 mg/ml LPS and yolk phospholipid fraction (FIG. 3). Cytokine inhibition was also determined by a modified assay to confirm the specific inhibition by yolk phospholipid fraction. In this assay, cells were incubated with 0.2 mg/ml LPS to induce TNFa and IL-1b. After 2 hr incubation, LPS in medium was removed by washing the cells. Cells were then incubated with yolk phospholipid fraction for two more hours. Consistently, both of TNFa and IL-1b were suppressed completely. In contrast, cells with LPS for 2 h incubation but no additional yolk phospholipid fraction thereafter showed high expression of TNFa and IL-1b.

Example 5

IL-2 Inhibition

It was also found that IL-2, another pro-inflammatory cytokine, was inhibited by yolk lipid fraction. IL-2 was inhibited by both the acetone extract and ethanol extract partially (FIG. 4). Due to impure composition of the neutral lipid, acetone extract could mix with certain portion of phospholipid fraction during the solvent extraction. By the same determination, yolk phospholipid fraction did not show any effects on the expressions of IL-6, IL-12, and TGFb in cells.

Example 6

Inhibition of PGE2 Biosyhthesis

The effect of yolk lipid fractions on the inhibition of PGE2 biosynthesis in mouse monocyte macrophage Experiment Many cell types are capable of expressing both COX-1 and COX-2; others express one or the other. The RAW 264.7 cells used in this assay express both isoforms of cyclooxygenase (demonstrated by immunofluoresence assays in our lab). The assay began with overnight induction of COX-2 through mitogenic (LPS) stimulation of RAW 264.7 cell monolayers. The cell monolayers were then exposed to a test article (e.g. indomethacin) for 30 min at 37° C., and then an exogenous source of arachidonic acid was provided to the system. COX1 and COX2 (in addition to a PGE2 specific synthetase) converted the exogenous arachidonic acid to PGE2. Prostaglandin E2 in the culture medium was then quantified by a commercial EIA system. When less PGE2 was recovered from culture medium containing a test article than was recovered from culture medium alone, the condition was labeled inhibition. The particular mechanism by which inhibition of PGE2 biosynthesis occurred in this assay cannot be deduced and would require further study.

Assay procedure: 5×106 Cells in DMEM medium were seeded and incubated in a 37° C., 5% CO2 incubator overnight. At approximately 24 h growth of cells seeded on day 1 (usually 90–100% confluence), growth medium was aseptically decanted and discarded. 10 ml sterile PBSA was gently pipetted into flasks against a non-growth surface, and the cells were washed twice. 10 ml DMEM containing LPS (2 ng/ml) was added to the tested flasks. Flasks were placed in a 37° C., 5% CO2 incubator overnight for 16 h.

At 16 h post-initial LPS exposure, growth medium was aseptically removed (suction) and discarded. 10 ml sterile PBSA was gently pipetted into flasks against a non-growth surface, and the cells were washed twice. Cells were incubated in the presence of 2 ml PBSA, 2 ml positive control drugs, or 2 ml yolk lipids sample (1.0 mg/ml) at 37° C. After 30 min incubation, 222 µl of 300 ΞM arachidonic acid was added to every flask. Cells were incubated for an additional 15 min at 37° C. in presence of the 30 µM arachidonic acid. After the 15 min incubation, 50 µl of 1 mg/ml indomethacin was added to contents of flask to stop the reaction. All fluids from flasks were collected into appropriately labeled polypropylene tubes.

Prostaglandin E2 was assayed with the commercial ELISA kit (Amersham RPN222) at room temperature following the standard protocol.

Result

PGE2 biosynthesis in this model was inhibited by various NSAID, such as indomethacin, aspirin, and ibuprofen (data not shown). It has been reported that the three NSAIDs are non-selected inhibitors to both enzymes of COX-1 and COX-2. They are considered as non-specific drugs, and in most cases, they caused side effects on clinical application to treat patients.

In our study, PGE2 biosynthesis in cells was inhibited by the yolk fractions at different levels (Table 2). In the crude materials, yolk showed to be more strong inhibition than whole egg on PGE2 biosynthesis. The inhibitory potency of both egg yolk and whole egg, however, was relative lower (17% in average) comparing to lipid fractions. Acetone extract and methanol extract of yolk lipids inhibited PGE2 biosynthesis to 31% and 54%, respectively. In contrast, both of the protein-enriched fractions, the water-soluble proteins (Filtrate) and the water-insoluble proteins (Residues), showed no inhibitions on PGE2 biosynthesis in cells. It is suggested that the active inhibitor of egg yolk to PGE2 biosynthesis is located in the phospholipids portion, and it is possible that the active component is a water-insoluble and non-peptide like molecule. This molecule may be a distinct molecule differs from the active component for inhibiting the cytokines expression. It is indicated that yolk phospholipid fraction has multiple modulators to suppress different pro-inflammatory molecules.

TABLE 2

Inhibition of $PGE_2$ biosynthesis in vitro by PL-100 egg fractions

| Fraction | Spray dried | | Fresh | | Mean |
| --- | --- | --- | --- | --- | --- |
| | Whole egg | Egg yolk | Whole egg | Egg yolk | |
| Start egg | −3 | 30 | 21 | 18 | 17 |
| Filtrate | −5 | −2 | 13 | −6 | 0 |
| Acetone extract | 16 | 82 | −19 | 43 | 31 |
| MeOH extract | 48 | 61 | 55 | 52 | 54 |
| Residues | −11 | 12 | −21 | 0 | −6 |

1. n = 5
2. The number represents % of inhibition of $PGE_2$ biosynthesis in vitro.
3. Concentration of egg fraction in tested cell culture was 1.0 mg/ml medium.

Example 7

Collagen-Induced Arthritis Model

Determination of anti-inflammatory effect of PL-100 yolk in collagen-induced arthritis model in rats.

Experiment

The method of inducing and evaluating collagen-induced arthritis in rats was according to the protocol developed by Trentham, et al. 1977 (8). PL-100 yolk and the delipidated fraction were fed to rats for 7 days prior to initiation of the type II collagen induced arthritis in rats and for 16 days after induction. A total 30 Sprague-Dawley(VAF+), female rats, 6–8 weeks of age (~125 g) were obtained from Charles River-VAF+. Three groups of rats (10 rats per group) were tested. They were control (water gavage), 3.5 ml of a 5% solution of egg yolk, and 3.5 ml of 5% delipidated yolk fraction. Rats were gavaged with samples every other day. The second day solutions were stored at 4° C. until use. After two days, excess solutions were discarded. Starting at 10 days after intradermal immunization and daily thereafter until day 21, rats were clinically evaluated (blindly) for rat paw erythema (0–4+) and paw swelling (0–4+). On day 21, all rats were sacrificed and bled.

Result

Hyperimmune egg yolk suppressed about 40% paw erythema and paw swelling of tested rats in a model of collagen-induced arthritis (FIG. 6). Comparing to yolk fraction, the delipidated yolk as well as control sample showed no effects on the created lesion. Even through this experiment lacked a yolk lipids group in the tested study to show the specific effect on the inhibition of inflammation, the indirect result indicated that yolk phospholipid fraction contained the anti-inflammatory components.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A composition comprising a substantially purified Cytokine Inhibitory Factor, wherein the Cytokine Inhibitory Factor:
   a) has molecular weight less than 6,000 Da;
   b) is naturally present in a lipid fraction of egg yolk of avian eggs;
   c) has a maximum wavelength absorbance at 205 nm;
   d) is a non-proteinatious substance;
   e) has a melting point of between about 39° C. to 42° C.; and
   f) inhibits RNA transcription of tumor necrosis factor alpha (TNF -α), interleukin-1-beta (IL-1β), and interleukin-2 (IL-2).

2. The composition of claim 1 wherein the Cytokine Inhibitory Factor is soluble in a solvent selected from the group consisting of chloroform, ethanol, and methanol.

3. The composition of claim 1 wherein 100 mg of the Cytokine Inhibitory Factor is soluble in 1.0 milliliters of solvent.

4. The composition of claim 1 wherein the Cytokine Inhibitory Factor is insoluble in a solvent selected from the group consisting of acetone, DMSO, hexane, diethyl ether, vegetable oil, and water.

5. The composition of claim 1 wherein the Cytokine Inhibitory Factor inhibits biosynthesis of prostaglandin $E_2$ ($PGE_2$).

6. The composition of claim 1 wherein the Cytokine Inhibitory Factor has an anti-inflammatory effect in treating arthritis.

7. The composition of claim 1 wherein the composition comprises a pharmaceutically acceptable carrier.

8. The composition of claim 7 wherein the pharmaceutically acceptable carrier is selected from the group consisting of: water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells, and cellular membranes.

9. The composition of claim 7, wherein said pharmaceutically acceptable carrier is a hyperimmune egg product which is selected to be enriched for said Cytokine Inhibitory Factor.

10. The composition of claim 7, wherein said pharmaceutically acceptable carrier is a food product produced with at least a fraction of a hyperimmune egg product, wherein said fraction comprises an enriched amount of said Cytokine Inhibitory Factor as compared to said hyperimmune egg product.

11. The composition of claim 7, wherein said pharmaceutically acceptable carrier comprises a fraction of a hyperimmune egg product containing an enriched amount of said Cytokine Inhibitory Factor as compared to said hyperimmune egg product.

12. The composition of claim 11, wherein said fraction is selected from the group consisting of: liquid egg yolk, powdered egg yolk, and a water in-soluble fraction of said hyperimmune egg product.

13. The composition of claim 7, wherein said composition is in a form selected from the group consisting of a liquid, an aerosol, a capsule, a tablet, a pill, a powder, a gel and a granule.

14. The composition of claim 7, wherein said pharmaceutically acceptable carrier comprises a controlled release formulation.

15. A purified Cytokine Inhibitory Factor produced by a process comprising:

a) separating a water-insoluble fraction (WIF) from a water-soluble fraction (WSF) of an egg yolk;

b) separating the water-insoluble fraction into a neutral lipid fraction and a polar lipid fraction;

c) purifying the polar lipid fraction into Cytokine Inhibitory Factor fractions by high performance liquid chromatography.

16. The purified Cytokine Inhibitory Factor of claim 15 wherein step b) the neutral lipid fraction is extracted using an organic solvent selected from the group consisting of acetone and hexane.

17. The purified Cytokine Inhibitory Factor of claim 15 wherein step b) the polar lipid fraction is extracted using an organic solvent selected from the group consisting of ethanol, chloroform, and methanol.

18. A method for purifying a Cytokine Inhibitory Factor from an avian egg, the egg comprising a yolk and a white, the method comprising:

a) separating the egg into a water-insoluble fraction (WIF) and a water-soluble fraction (WSF);

b) extracting a polar lipid fraction from the water-insoluble fraction and;

c) purifying the polar lipid fraction into Cytokine Inhibitory Factor fractions by high performance liquid chromatography.

19. The method of claim 18 further comprising extracting a neutral lipid fraction from the water-insoluble fraction of the egg.

20. The method of claim 18 wherein step b) is performed by supercritical fluid extraction.

21. The method of claim 18 further comprising separating the egg yolk from the egg white, wherein step a), the egg yolk is separated into the water-insoluble fraction (WIF) and the water-soluble fraction (WSF).

22. A method of inhibiting Cytokine expression in an animal comprising administering the composition of claim 1 to the animal.

23. The method of claim 22 wherein the cytokine comprises a proinflammatory cytokine selected from the group consisting of tumor necrosis factor alpha (TNF-$\alpha$), interleukin-1-beta (IL-1$\beta$), and interleukin-2 (IL-2).

24. The method of claim 22 wherein the composition comprises a pharmaceutically acceptable carrier.

25. The method of claim 24 wherein the pharmaceutically acceptable carrier is selected from the group consisting of: water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells, and cellular membranes.

26. The method of claim 22 wherein the composition is administered by a route selected from the group consisting of oral, intravenous administration, intraperitoneal administration, intramuscular administration, subcutaneous administration, transdermal delivery, intratracheal administration, inhalation, impregnation of a catheter, by suppository, and direct injection into a tissue.

27. The method of claim 22, wherein said composition is administered at a dose of from about 1 nanogram to about 400 milligrams of said Cytokine Inhibitory Factor per kilogram body weight of said animal.

28. The method of claim 22, wherein administration of said composition inhibits expression of tumor necrosis factor-alpha (TNF-$\alpha$), interleukin-1$\beta$(IL-1$\beta$) or interleukin-6 (IL-6) by cells of said animal.

29. The method of claim 22, wherein administration of said composition down regulates synthesis of prostaglandin $E_2$ ($PGE_2$) by cells of said animal.

30. The method of claim 22, wherein the animal is a mammal.

31. A method of modulating the immune system of an animal, comprising administering to the animal a composition comprising a Cytokine Inhibitory Factor, wherein the Cytokine Inhibitory Factor:

a) has molecular weight less than 6,000 Da;

b) is naturally present in a lipid fraction of egg yolk of avian eggs;

c) has a maximum wavelength absorbance at 205 nm;

d) is a non-proteinatious substance;

e) has a melting point of between about 39° C. to 42° C.; and f) inhibits RNA transcription of tumor necrosis factor alpha (TNF-$\alpha$), interleukin-1-beta (IL-1$\beta$), and interleukin-2 (IL-2).

32. The method of claim 31, wherein said composition is administered by a route selected from the group consisting of oral, intravenous administration, intraperitoneal administration, intramuscular administration, subcutaneous administration, transdermal delivery, intratracheal administration, inhalation, impregnation of a catheter, by suppository, and direct injection into a tissue.

33. The method of claim 31, wherein said composition comprises a food product containing said Cytokine Inhibitory Factor.

34. The method of claim 31, wherein administration of said composition produces a result selected from the group consisting of: reduction in symptoms of arthritis and reduction of inflammation associated with arthritis.

* * * * *